United States Patent
Comely et al.

(10) Patent No.: US 7,902,355 B2
(45) Date of Patent: Mar. 8, 2011

(54) PROCESS FOR THE PREPARATION OF AN 11-(4-SUBSTITUTED-1-PIPERAZINYL) DIBENZO[B,F][1,4]THIAZEPINE DERIVATIVE

(75) Inventors: Alexander Christian Comely, Barcelona (ES); Francesc Xavier Verdaguer Espaulella, Vic (ES); Llorenç Rafecas Jané, Llorenç del Penedès (ES); Antonio Domingo Coto, Barcelona (ES)

(73) Assignee: Union Quimico-Farmaceutica S.A., Barcelona (ES)

( * ) Notice: Subject to any disclaimer, the term of this patent is extended or adjusted under 35 U.S.C. 154(b) by 768 days.

(21) Appl. No.: 11/817,884

(22) PCT Filed: Dec. 21, 2005

(86) PCT No.: PCT/EP2005/014055
§ 371 (c)(1), (2), (4) Date: Sep. 6, 2007

(87) PCT Pub. No.: WO2006/094549
PCT Pub. Date: Sep. 14, 2006

(65) Prior Publication Data
US 2008/0171869 A1    Jul. 17, 2008

(30) Foreign Application Priority Data
Mar. 7, 2005 (ES) .................................. 200500513

(51) Int. Cl.
*C07D 281/16* (2006.01)
(52) U.S. Cl. ...................................................... 540/551
(58) Field of Classification Search .................. 540/551
See application file for complete search history.

(56) References Cited

FOREIGN PATENT DOCUMENTS
EP    0 240 228 A    10/1987

OTHER PUBLICATIONS
International Search Report for Application No. PCT/EP2005/014055, mailed Jun. 13, 2006.

*Primary Examiner* — Brenda L Coleman
(74) *Attorney, Agent, or Firm* — Day Pitney LLP

(57) ABSTRACT

A process for the preparation of an 11-(4-substituted-1-piperazinyl)dibenzo[b,f][1,4]thiazepine derivative, of general Formula (I), where A is hydrogen or a —$(CH_2)_2$—OH group or a —$(CH_2)_2$-0-$(CH_2)_2$—OH group, or of a salt thereof, comprises a step in which 10H-dibenzo[b,f][1,4]thiazepin-11-one is reacted with a piperazine derivative in the presence of a titanium alkoxide of general formula $Ti(OR)_4$, where R is a straight or branched alkyl group, having from one to eight carbon atoms to obtain said Formula I derivative or a salt thereof. Where A is —$(CH_2)_2$-0-$(CH_2)_2$—OH, then the piperazine derivative is 1-(2-(2-hydroxyethoxy)ethyl)piperazine and the 11-(4-substituted-1-piperazinyl)dibenzo[b,f][1,4]thiazepine is quetiapine, (11-(4-(2-(2-hydroxyethoxy)ethyl)-1-piperazinyl)dibenzo[b,f][1,4]thiazepine). The process may comprise an additional step of reacting the quetiapine with fumaric acid to obtain quetiapine hemifumarate.

(I)

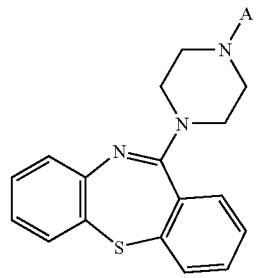

22 Claims, No Drawings

PROCESS FOR THE PREPARATION OF AN 11-(4-SUBSTITUTED-1-PIPERAZINYL) DIBENZO[B,F][1,4]THIAZEPINE DERIVATIVE

This application is a national stage entry under 35 U.S.C. §371 of PCT/EP05/14055, filed Dec. 21, 2005.

FIELD OF THE INVENTION

The invention relates to a process for the preparation of an 11-(4-substituted-1-piperazinyl)dibenzo[b,f][1,4]thiazepine derivative, of general formula I

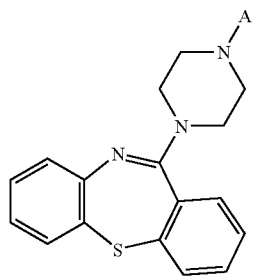

I where A is hydrogen or a —(CH$_2$)$_2$—OH group or a —(CH$_2$)$_2$—O—(CH$_2$)$_2$—OH group, or of a salt thereof.

When A is the —(CH$_2$)$_2$—O—(CH$_2$)$_2$—OH group, the Formula I compound is quetiapine, a compound known for its dopamine antagonist activity and which may be used as an antipsychotic agent, as a neuroleptic, or in the treatment of hyperactivity, having a notable reduction in some undesirable side effects associated with other active ingredients of the same therapeutical category. On the other hand, when A is hydrogen, the Formula I compound is useful as an intermediate for the preparation of quetiapine itself, as disclosed in EP 0 282 236 B1, and when A is —(CH$_2$)$_2$—OH, the Formula I compound may be easily converted into advanced intermediates for the synthesis of quetiapine, according to the process disclosed in WO 01/055215 A1.

STATE OF THE ART

Several processes are known for the synthesis of 11-(4-substituted-1-piperazinyl)dibenzo[b,f][1,4]thiazepine derivatives, of general formula I, and in particular of quetiapine. For example, in EP 0 240 228 B1 two alternative processes for the synthesis of quetiapine (see schemes 1 and 2) are described.

Scheme 1

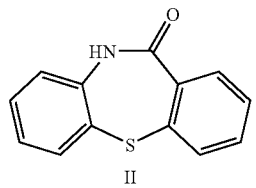

II

↓ POCl$_3$

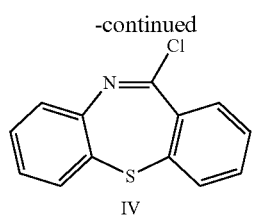

IV

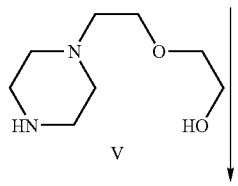

V

↓

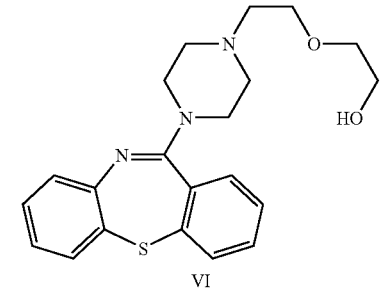

VI

In general these processes start out from 10H-dibenzo-[b,f][1,4]thiazepin-11-one, of Formula II, and require the synthesis of an halogenated intermediate, of Formula IV, or a sulphur derivative, of Formulas VII or XI.

Scheme 2

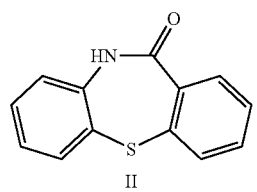

II

↓ P$_2$S$_5$

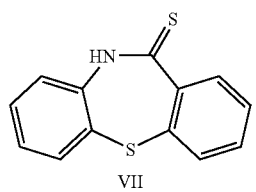

VII

↓ RI

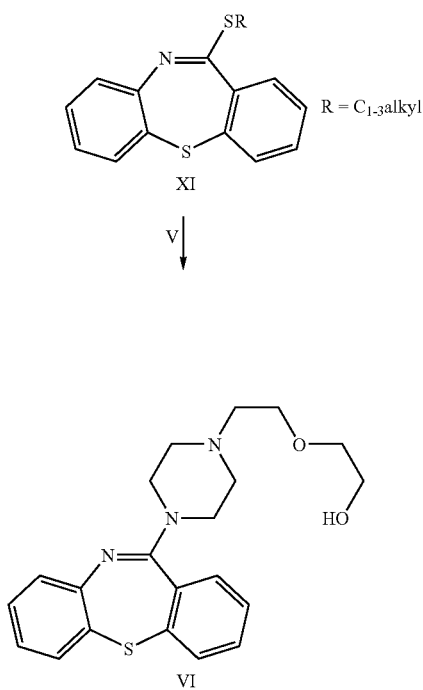

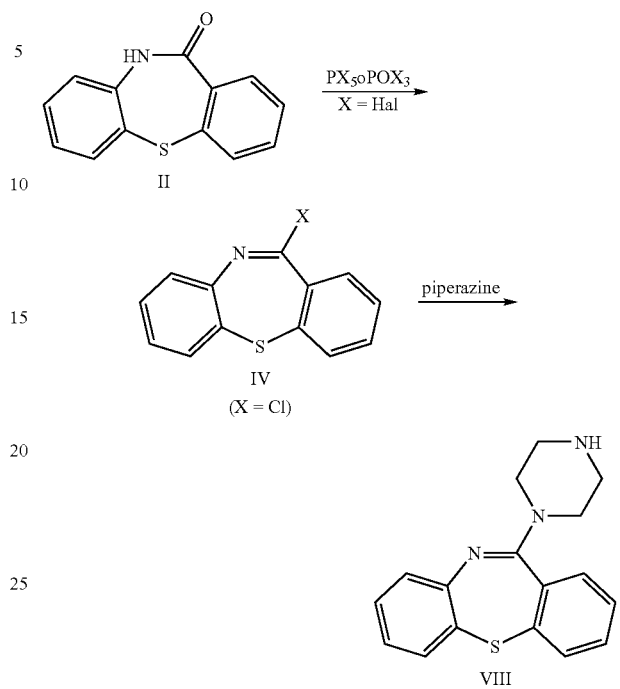

The Formula II compound is known and the preparation thereof is described, for example, by J. Schmutze et al. *Helv. Chim. Acta,* 48, 336 (1965).

EP 0 282 236 B1 describes a another process for the synthesis of quetiapine, starting out from the intermediate 11-(1-piperazinyl)dibenzo[b,f][1,4]thiazepine, of Formula VIII (see Scheme 3)

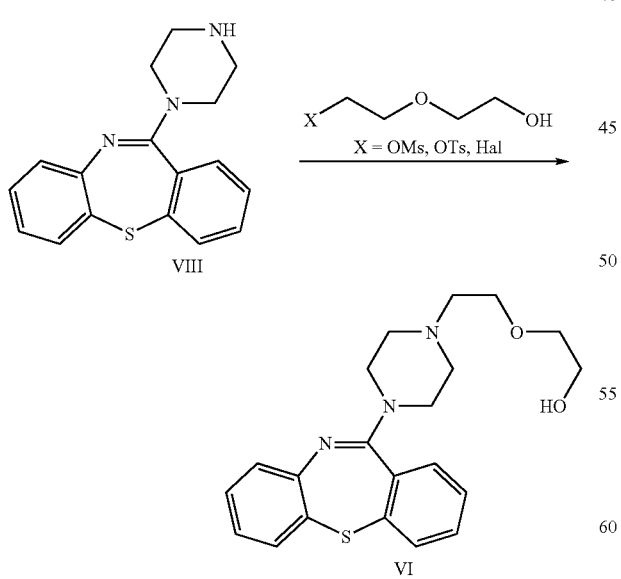

Nevertheless, the preparation of said Formula VIII compound again requires the synthesis of a halogenated intermediate (see Scheme 4)

WO 2004/076431 A1 describes a variant synthesis of Scheme 3 in which a phase transfer catalyst is used.

WO 01/055215 describes another process for the preparation of quetiapine where an 11-(4-(2-haloethyl)-1-piperazinyl)dibenzo[b,f][1,4]thiazepine, prepared by ring formation from bicyclic structures, is condensed with ethylene glycol in the presence of metallic sodium.

SUMMARY OF THE INVENTION

It is an object of the invention to provide a new synthetic process for the preparation of an 11-(4-substituted-1-piperazinyl)dibenzo[b,f][1,4]thiazepine derivative of general Formula I,

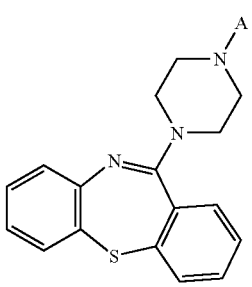

where A is hydrogen or a —$(CH_2)_2$—OH group or a —$(CH_2)_2$—O—$(CH_2)_2$—OH group, or of a salt thereof, comprising a step in which 10H-dibenzo-[b,f][1,4]thiazepin-11-one of Formula II,

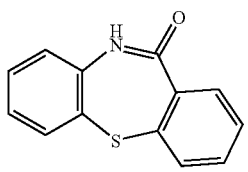

II is directly reacted with a piperazine derivative, of general Formula III,

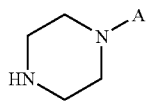

III where A has the same meaning as given above, in the presence of a titanium alkoxide, of the general Formula Ti(OR)$_4$, where R is a straight or branched C$_1$-C$_8$ alkyl, to obtain said Formula I derivative or a salt thereof.

In the process of the invention, the direct reaction of an amide with an amine to give an amidine is unexpected and surprising. The present inventors have found very few examples related in the scientific literature and in none of them is a titanium alkoxide used as condensation agent for this type of reactions. The reaction proceeds at a high temperature, above 100° C., and the titanium alkoxide acts simultaneously as reactive agent and solvent.

The process according to the invention effectively affords a number of advantages.

a) Reduction of Synthesis Steps.

The direct reaction between the Formula II compound and the piperazine derivative of general Formula III allows the number of synthesis steps to be reduced in comparison with the known prior art processes. For example, some of the known prior art processes stated above are, in summary:

EP 0 240 228 B1 i II+POCl$_3$=IV
ii IV+V=VI (quetiapine)
or i II+P$_2$S$_5$=VII
ii VII+CH$_3$I=XI (R=CH$_3$)
iii XI+V=VI (quetiapine)
EP 0 282 236 B1 i. II+POCl$_3$=IV
ii. IV+piperazine=VIII
iii. VIII+ClCH$_2$CH$_2$OCH$_2$CH$_2$OH=VI (quetiapine)

b) Convergence

In the process of the invention, the Formula II compound and the piperazine derivative are combined in the final synthesis step. This is particularly advantageous since both products have a high added value, and in this way their use is optimized by reducing the losses for the yields in the different steps.

c) Lower Consumption of the Piperazine Derivative Equivalents

In the process of the invention, there is avoided the need to use, at least, two equivalents of the piperazine derivative, with a view to neutralizing the hydrogen chloride formed as by-product in the processes using the chlorinated derivative of Formula IV. This allows the consumption of said piperazine derivative to be reduced.

d) Working Conditions and Environemental Effects

In the prior art processes it is always necessary to use highly toxic and hazardous reactants, such as for example phosphorous oxichloride, phosphorous pentachloride or phosphorous pentasulfide. Also to be highlighted is the generation of toxic by-products such as, for example, hydrogen chloride, methylmercaptan, phosphoric acid or hydrochloric acid. Nevertheless, in the process of the invention, both the reactive agent used, a titanium alkoxide, and the by-products formed, titanium dioxide and a lower alcohol, are much easier to handle, have low toxicity, are not chlorinated and are much less harmful for the environment.

DETAILED DESCRIPTION OF EMBODIMENTS OF THE INVENTION

The new process for the preparation of a Formula I derivative consists of the direct condensation between 10H-dibenzo[b,f][1,4]thiazepin-11-one, of Formula II, and a piperazine derivative, of Formula III in the presence of a titanium alkoxide of formula Ti(OR)$_4$, where R is a straight or branched alkyl group, having from one to eight carbon atoms (see Scheme 5).

Advantageously, the titanium alkoxide, of formula Ti(OR)$_4$, is added at a rate of 1 to 8 equivalents for each equivalent of the Formula II compound, preferably at a rate of 1.5 to 4 equivalents for each equivalent of the Formula II compound, and most preferably at a rate of 2.8 to 3.2 equivalents for each equivalent of the Formula II compound. Preferably R is ethyl, isopropyl or n-butyl.

Advantageously, the piperazine derivative, of Formula III, is added at a rate of 1.5 to 4 equivalents for each equivalent of the Formula II compound, preferably at a rate of 1.8 to 2.2 equivalents for each equivalent of the Formula II compound.

Advantageously, the molar ratio between the titanium alkoxide, of formula Ti(OR)$_4$, and the piperazine derivative, of Formula III, ranges from 1:1.5 to 5:1, preferably from 1:1.2 to 2.7:1 and most preferably from 1:1.1 and 1.8:1.

Advantageously, the reaction step of the Formula II compound with the piperazine derivative is conducted at a temperature ranging from 140° C. to 200° C., preferably from 160° C. to 190° C. and most preferably from 165° C. and 175° C. Advantageously the distillation, at least partial, of the alcohol generated during the reaction is carried out simultaneously during that step.

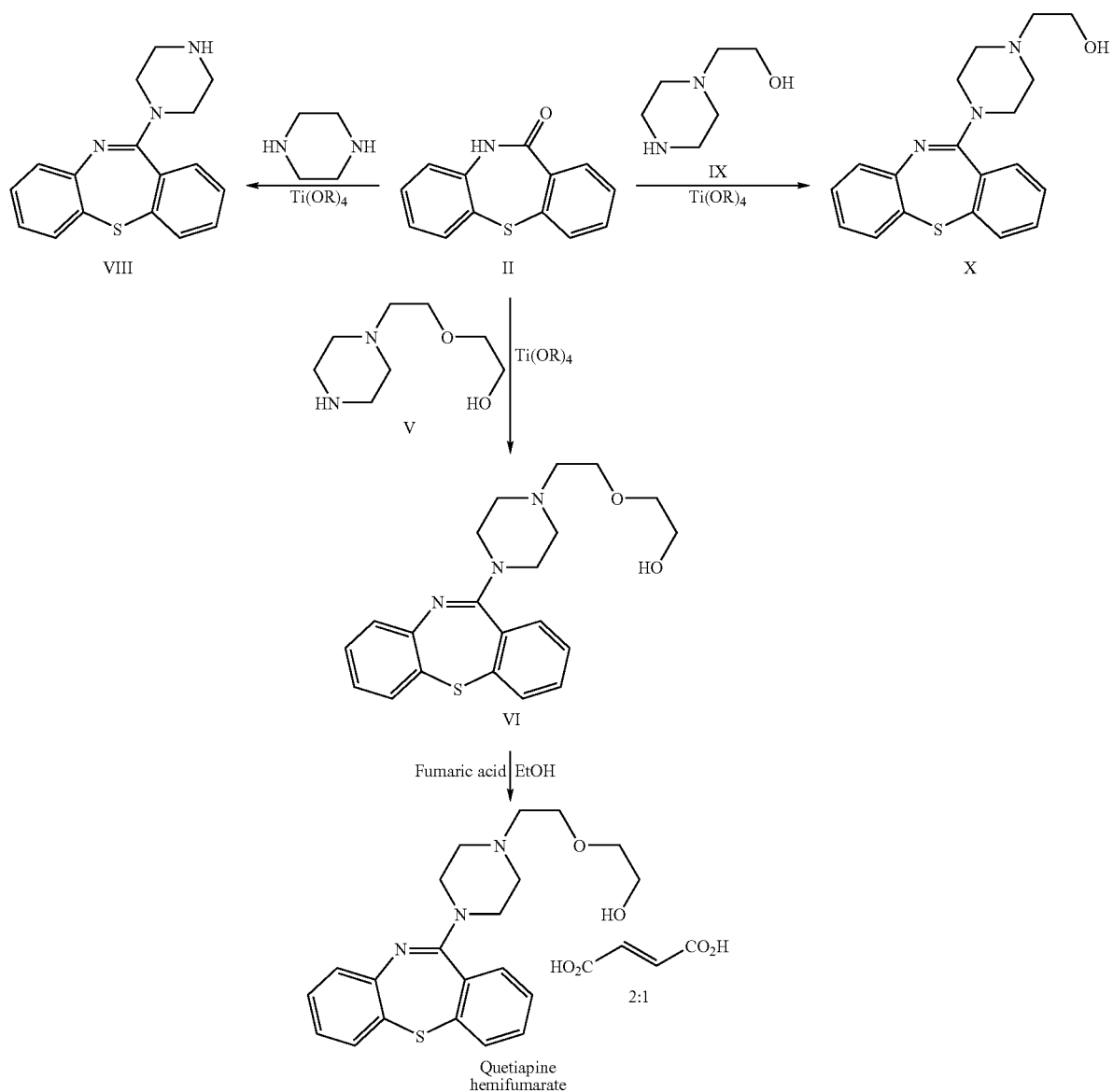

Optionally, at least one of the following compounds may be used as an additive: an alcohol having a boiling point above the reaction temperature, a molecular sieve, silica, acetic acid, pyridine, 2,6-dimethylpiperidine or 2-methylpiperidine. For example, when titanium tetramethoxide is used, a solid having a melting point of 200-210° C., it may be advantageous to use a high boiling point alcohol as diluent.

A particularly preferred embodiment of the process of the invention is obtained when, with R being isopropyl, the titanium tetraisopropoxide, of formula Ti(OiPr)$_4$, is added at a rate of 1.5 to 4 equivalents for each equivalent of the Formula II compound, the piperazine derivative, of Formula III, is added at a rate of 1.5 to 4 equivalents for each equivalent of the Formula II compound, the molar ratio between Ti(OiPr)$_4$, and the piperazine derivative ranges from 1:1.2 to 2.7:1, the reaction step is conducted at a temperature ranging from 160° C. to 190° C., with a reaction time ranging from 3 to 12 hours, and during said reaction step the isopropanol generated during the reaction is simultaneously distilled off, at least in part.

Another particularly preferred embodiment of the process of the invention is obtained when, with R being isopropyl, the titanium tetraisopropoxide, of formula Ti(OiPr)$_4$, is added at a rate of 2.8 to 3.2 equivalents for each equivalent of the Formula II compound, the piperazine derivative, of Formula III, is added at a rate of 1.8 to 2.2 equivalents for each equivalent of the Formula II compound, the molar ratio between Ti(OiPr)$_4$, and the piperazine derivative ranges from 1:1.1 to 1.8:1, the reaction step is conducted at a temperature ranging from 165° C. to 175° C., with a reaction time ranging from 4 to 6 hours, and during said reaction step the isopropanol generated during the reaction is simultaneously distilled off, at least in part.

Preferably, the piperazine derivative is 1-(2-(2-hydroxyethoxy)ethyl)piperazine, of Formula V,

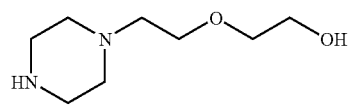

V and the 11-(4-substituted-1-piperazinyl)dibenzo[b,f][1,4]thiazepine derivative is 11-(4-(2-(2-hydroxyethoxy)ethyl)-1-piperazinyl)dibenzo[b,f][1,4]thiazepine (quetiapine) of Formula VI.

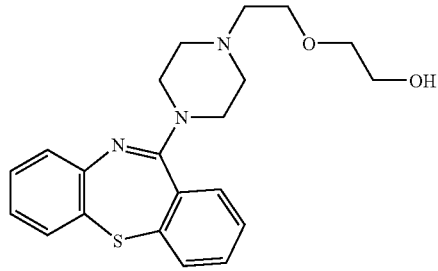

VI

This corresponds to the particular case in which, in the Formula I compound, A is —(CH$_2$)$_2$—O—(CH$_2$)$_2$—OH. Advantageously, the process comprises an additional step of reacting the quetiapine with fumaric acid to produce quetiapine hemifumarate.

Preferably, the piperazine derivative is piperazine, and the 11-(4-substituted-1-piperazinyl)dibenzo[b,f][1,4]thiazepine is 11-(1-piperazinyl)dibenzo[b,f][1,4]thiazepine, of Formula VIII.

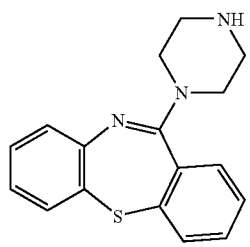

VIII

This corresponds to the particular case in which, in the Formula I compound, A is hydrogen.

Preferably the piperazine derivative is 1-(2-hydroxyethyl)piperazine, of Formula IX,

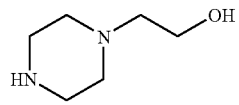

IX and the 11-(4-substituted-1-piperazinyl)dibenzo[b,f][1,4]thiazepine is 11-(4-(2-hydroxyethyl)-1-piperazinyl)dibenzo[b,f][1,4]thiazepine, of Formula X,

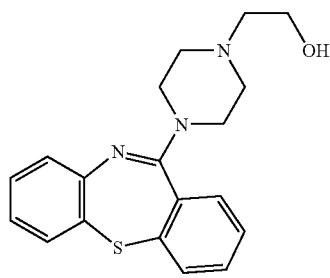

X

This corresponds to the particular case in which, in the Formula I compound, A is —(CH$_2$)$_2$—OH.

EXAMPLES

Example 1

To a mixture of 10H-dibenzo-[b,f][1,4]thiazepin-11-one (II) (68.1 g, 300 mmol) and 1-(2-(2-hydroxyethoxy)ethyl)piperazine (V) (157 g, 900 mmol) there was added titanium tetraisopropoxide (247 ml, 830 mmol) under an inert atmosphere. The resulting suspension was heated to 170° C. and the isopropanol generated during the reaction was removed by distillation.

When the distillation seemed to terminate, a gentle vacuum was applied for 5 minutes to complete it. After 6 hours reaction, the mixture was cooled to 100° C. and diluted with toluene. The titanium reactive agent was destroyed with an excess of water and the precipitate was filtered off. After washing the residue twice with toluene, the combined filtrates were washed twice with water and concentrated under vacuum to give quetiapine (V) (98.5 g, 86%) as a viscous yellow oil.

IR 3398, 2919, 2855, 1597, 1575, 1558, 1456, 1437, 1306, 1250, 1244, 1118, 1063, 1014, 762 and 742 cm$^{-1}$.

$^1$H NMR (400 MHz, CDCl$_3$) 7.52-7.49 (m, 1H), 7.40-7.37 (m, 1H), 7.35-7.28 (m, 3H), 7.19-7.15 (m, 1H), 7.08-7.05 (m, 1H), 6.90-6.86 (m, 1H), 3.71-3.61 (m, 10H), 3.50 (brs, 1H), 2.65-2.62 (m, 4H) and 2.58-2.54 (m, 2H).

$^{13}$C NMR (101 MHz, CDCl$_3$) 160.6, 148.9, 140.0, 134.1, 132.2, 132.1, 130.8, 129.1, 128.9, 128.3, 127.9, 125.3, 122.8, 72.4, 67.7, 62.0, 58.0, 53.1 and 46.5.

m/z (EI) 383 (M$^+$, 4%), 321 (M-HOCH$_2$CH$_2$OH, 50), 239 (M-HOCH$_2$CH$_2$OH—HOCH$_2$, 65) and 210 (dibenzothiazepine-H, 100).

Example 2

To a mixture of 10H-dibenzo-[b,f][1,4]thiazepin-11-one (II) (454 mg, 2 mmol) and 1-(2-(2-hydroxyethoxy)ethyl)piperazine (V) (522 mg, 3 mmol) there was added titanium tetraisopropoxide (2.4 ml, 8 mmol) under an inert atmosphere. The resulting suspension was heated to 200° C. and the isopropanol generated during the reaction was removed by distillation. After 20 hours reaction, the mixture was cooled to 100° C. and diluted with toluene. The titanium reactive agent was destroyed with an excess of water and the precipitate was removed from the mixture by filtration. After washing the residues twice with toluene, the combined filtrates were washed twice with water and concentrated under vacuum to give quetiapine (VI) (465 mg, 61%) as a viscous yellow oil having identical characteristics as those described for Example 1.

Example 3

To a mixture of 10H-dibenzo-[b,f][1,4]thiazepin-11-one (II) (22.7 g, 100 mmol) and 1-(2-(2-hydroxyethoxy)ethyl)piperazine (V) (31.3 g, 180 mmol) there was added titanium tetraisopropoxide (50.5 ml, 170 mmol) under an inert atmosphere. The resulting suspension was heated to 170° C. and the isopropanol generated during the reaction was removed by distillation. When the distillation was ending, a gentle vacuum was applied for 5 minutes to complete the distillation. After 6 hours total reaction time, the mixture was cooled to 100° C. and diluted with toluene. The titanium reactive agent was destroyed with an excess of water and the precipitate was removed from the mixture by filtration. After washing the residues twice with toluene, the combined filtrates were washed twice with water and concentrated under vacuum to give quetiapine (VI) (35.9 g, 94%) as a viscous yellow oil having identical characteristics as those described for Example 1.

Example 4

To a mixture of 10H-dibenzo-[b,f][1,4]thiazepin-11-one (II) (68.1 g, 300 mmol) and 1-(2-(2-hydroxyethoxy)ethyl)piperazine (V) (104.4 g, 600 mmol) there was added titanium tetraisopropoxide (268 ml, 900 mmol) under an inert atmosphere. The resulting suspension was heated to 170° C. and the isopropanol generated during the reaction was removed by distillation. When the distillation was ending, a gentle vacuum was applied for 5 minutes to complete the distillation. After 6 hours total reaction time, the mixture was cooled to 100° C. and diluted with toluene. The titanium reactive agent was destroyed with an excess of water and the precipitate was removed from the mixture by filtration. After washing the residues twice with toluene, the combined filtrates were washed twice with water and concentrated under vacuum to give quetiapine (V) (100.0 g, 87%) as a viscous yellow oil having identical characteristics as those described for Example 1.

Example 5

To a mixture of 10H-dibenzo-[b,f][1,4]thiazepin-11-one (II) (2.27 g, 10 mmol), 1-(2-(2-hydroxyethoxy)ethyl)piperazine (V) (2.61 g, 15 mmol) and 1-heptanol (4.2 ml, 30 mmol) there was added titanium tetraisopropoxide (8.0 ml, 27 mmol) under an inert atmosphere. The resulting suspension was heated to 160° C. and the isopropanol generated during the reaction was removed by distillation. After 32 hours the mixture was cooled to 100° C. and diluted with toluene. The titanium reactive agent was destroyed with an excess of water and the precipitate was removed from the mixture by filtration. After washing the residues with toluene, the combined filtrates were washed with water and concentrated under vacuum to give a mixture of quetiapine (VI) and 1-heptanol (4.24 g) as a yellow oil. The quetiapine was isolated as the hemifumarate salt thereof (2.295 g, 75%) after crystallization with the process described herebelow.

Example 6

To a solution of quetiapine (VI) (82.5 g, 215 mmol) in ethanol (660 ml) there was added fumaric acid (12.49 g, 108 mmol) and the mixture was heated under reflux for 2 hours in an inert atmosphere. A precipitate out of the solution formed shortly after starting the heating. After cooling the mixture to 0° C., it was filtered, washed with ethanol (250 ml, 0° C.) and dried at reduced pressure to give quetiapine hemifumarate (77.4 g, 81%) as a crystalline white solid.

Melting point: 173-175° C.
IR 3315, 2944, 2869, 1600, 1572, 1459, 1413, 1335, 1306, 1130, 1082, 1064, 989, 794 and 768 cm$^{-1}$.

$^1$H NMR (400 MHz, CDCl$_3$/CD$_3$OD) 7.52 (d, J=7.6 Hz, 1H), 7.40 (dd, J=8.0 and 1.6 Hz, 1H), 7.38-7.31 (m, 2H), 7.19 (m, 1H), 7.08 (dd, J=8.0 and 1.2 Hz, 1H), 6.92 (m, 1H), 6.78 (s, 1H), 3.87 (s, 4H), 3.73 (m, 2H), 3.67 (m, 2H), 3.55 (m, 2H), 3.03 (brm, 2H) and 2.94-2.89 (m, 4H).
$^{13}$C NMR (101 MHz, CDCl$_3$/CD$_3$OD) 170.1, 160.3, 148.3, 139.8, 135.1, 133.4, 132.11, 132.09, 131.1, 129.1, 128.8, 128.5, 127.9, 125.1, 123.3, 72.5, 65.9, 61.0, 57.2, 52.1 and 45.1.
m/z (Cl, NH$_3$) 384 (MH$^+$, 100%).

Example 7

To a mixture of 10H-dibenzo-[b,f][1,4]thiazepin-11-one (II) (2 g, 8.8 mmol) and piperazine (2.27 g, 26.4 mmol) there was added titanium tetraisopropoxide (7.0 ml, 25.8 mmol) under an inert atmosphere. The resulting suspension was heated to 170° C. and the isopropanol generated during the reaction was removed by distillation. After 5 hours the mixture was cooled to 100° C. and diluted with toluene. The titanium reactive agent was destroyed with an excess of water and the precipitate was removed from the mixture by filtration. After washing the residues with toluene, the combined filtrates were washed with water and concentrated under vacuum to give 11-(1-piperazinyl)dibenzo-[b,f][1,4-thiazepine (VIII) (2.58 g, 99%) as a viscous yellow oil. After purification by silica gel column chromatography (eluent: dichloromethane to dichloromethane/methanol 95:5), 1.55 g (60%) of 11-(1-piperazinyl)dibenzo-[b,f][1,4]-thiazepine (VIII) of high purity were obtained as a colourless viscous oil.

Rf (SiO$_2$, CH$_2$Cl$_2$/MeOH 9:1) 0.13
IR 3316, 3051, 2940, 2846, 1596, 1573, 1555, 1474, 1453, 1409, 1318, 1301, 1243, 1141, 1018, 762 and 741 cm$^{-1}$.
$^1$NMR (400 MHz, CDCl$_3$) 7.52-7.49 (m, 1H), 7.39 (dd, J=7.6 and 1.6 Hz, 1H), 7.34-7.28 (m, 3H), 7.19-7.14 (m, 1H), 7.07 (dd, J 8.0 and 1.2 Hz, 1H), 6.88 (ddd, J=7.2, 7.2 and 1.6 Hz, 1H), 3.49 (brs, 4H), 2.97 (brs, 2H), 2.92-2.86 (m, 2H) and 1.91 (brs, 1H).
$^{13}$C NMR (101 MHz, CDCl$_3$) 161.0, 148.9, 139.9, 134.1, 132.11, 132.09, 130.7, 129.0, 128.9, 128.2, 127.9, 125.3, 122.7, 48.0 and 45.9.
m/z (Cl, NH$_3$) 296 (MH$^+$, 100%) and 227 (dibenzothiazepine-H/NH$_3$, 16).

Example 8

To a mixture of 10H-dibenzo-[b,f][1,4]thiazepin-11-one (II) (2.2 g, 9.7 mmol) and 1-(2-hydroxyethyl)piperazine (IX) (2.5 g, 19.2 mmol) there was added titanium tetraisopropoxide (9.0 ml, 30.3 mmol) under an inert atmosphere. The resulting suspension was heated to 170° C. and the isopropanol generated during the reaction was removed by distillation. After 5.5 hours the mixture was cooled to 100° C. and diluted with toluene. The titanium reactive agent was destroyed with an excess of water and the precipitate was removed from the mixture by filtration. After washing the residues with toluene, the combined filtrates were washed with water and concentrated under vacuum to give 11-(4-(2-hydroxyethyl)-1-piperazinyl)dibenzo-[b,f][1,4-thiazepine (X) (3.0 g, 91%) as a yellow oil. After purification by silica gel column chromatography (eluent: dichloromethane to dichloromethane/methanol 97:3), 1.64 g (50%) of 11-(4-(2-hydroxyethyl)-1-piperazinyl)dibenzo-[b,f][1,4-thiazepine (X) of high purity were obtained as a colourless viscous oil.

Rf (SiO$_2$, CH$_2$Cl$_2$/MeOH 9:1) 0.43
IR 3406, 2936, 2814, 1598, 1574, 1453, 1408, 1305, 1256, 1146, 1061, 1011, 762 and 741 cm$^{-1}$.

H NMR (400 MHz, CDCl$_3$) 7.52-7.50 (m, 1H), 7.39 (dd, J=7.6 and 1.2 Hz, 1H), 7.35-7.27 (m, 3H), 7.19-7.15 (m, 1H), 7.08 (dd, J=8.0 and 1.6 Hz, 1H), 6.88 (ddd, J=7.6, 7.6 and 1.6 Hz, 1H), 3.65 (t, J=5.6 Hz, 2H), 3.56 (brs, 4H), 2.64 (brs, 1H) and 2.61-2.52 (m, 6H).

$^{13}$C NMR (101 MHz, CDCl$_3$) 160.7, 148.8, 139.9, 134.1, 132.1, 130.8, 129.1, 128.9, 128.2, 127.9, 125.3, 122.9, 59.4, 57.7, 52.7, 46.8 and 29.6.

m/z (CI, NH$_3$) 340 (MN$^+$, 100%) and 228 (dibenzothiazepine/NH$_3$, 21).

The invention claimed is:

1. A process for the preparation of an 11-(4-substituted-1-piperazinyl)dibenzo[b,f][1,4]thiazepine, of formula I

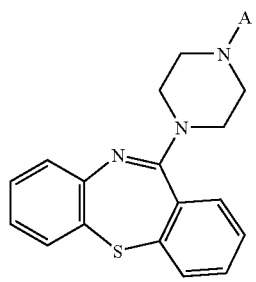

where A is hydrogen or a —(CH$_2$)$_2$—OH group or a —(CH$_2$)$_2$—O—(CH$_2$)$_2$—OH group, or of a salt thereof, comprising a step in which 10H-dibenzo-[b,f][1,4]-thiazepin-11-one of Formula II,

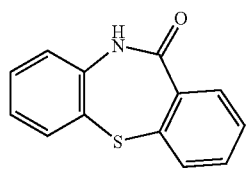

is directly reacted with a piperazine, of Formula III,

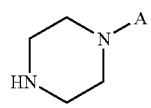

where A has the same meaning as given above, in the presence of a titanium alkoxide, of the Formula Ti(OR)$_4$, where R is a straight or branched alkyl, having one to eight carbon atoms, to obtain said Formula I or a salt thereof.

2. The process of claim 1 wherein R is ethyl, isopropyl, or n-butyl.

3. The process of claim 1 wherein R is isopropyl.

4. The process of claim 1, wherein said titanium alkoxide, of formula Ti(OR)$_4$, is added at a rate of 1 to 8 equivalents for each equivalent of the Formula II compound.

5. The process of claim 1, wherein said piperazine, of Formula III, is added at a rate of 1.5 to 4 equivalents for each equivalent of the Formula II compound.

6. The process of claim 1, wherein the molar ratio between said titanium alkoxide, of formula Ti(OR)$_4$, and said piperazine, of Formula III, ranges from 1:1.5 to 5:1.

7. The process of claim 1, wherein said step is conducted at a temperature ranging from 140° C. to 200° C.

8. The process of claim 1, wherein a distillation, at least partial, of the alcohol generated as by-product during the reaction is carried out simultaneously during said step.

9. The process of claim 1, wherein there is added as additive an alcohol having a boiling point above the reaction temperature, a molecular sieve, silica, acetic acid, pyridine, 2,6-dimethylpiperidine or 2-methylpiperidine.

10. The process of claim 1, wherein R is isopropyl, said titanium tetraisopropoxide, of formula Ti(OiPR)$_4$, is added at a rate of 1.5 to 4 equivalents for each equivalent of the Formula II compound, said piperazine, of Formula III, is added at a rate of 1.5 to 4 equivalents for each equivalent of the Formula II compound, said molar ratio between Ti(OiPR)$_4$ and said piperazine ranges from 1:1.2 to 2.7:1, said step is conducted at a temperature ranging from 106° C. to 190° C., said step has a reaction time ranging from 3 to 12 hours, and during said step there is carried out simultaneously the at least partial distillation of the isopropanol generated during the reaction.

11. The process of claim 1, wherein when R is isopropyl, said titanium tetraisopropoxide, of formula Ti(OiPR)$_4$, is added at a rate of 2.8 to 3.2 equivalents for each equivalent of the Formula II compound, said piperazine, of Formula III, is added at a rate of 1.8 to 2.2 equivalents for each equivalent of the Formula II compound, said molar ratio between Ti(OiPR)$_4$ and said piperazine ranges from 1:1.1 to 1.8:1, said step is conducted at a temperature ranging from 165° C. to 175° C., said step has a reaction time ranging from 4 to 6 hours, and during said step there is carried out simultaneously the at least partial distillation of the isopropanol generated during the reaction.

12. The process of claim 1, wherein said piperazine is 1-(2-(2-hydroxyethoxy)ethyl)piperazine, of Formula V:

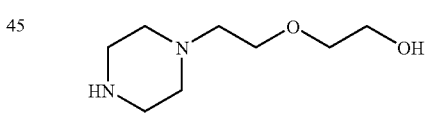

and said 11-(4-substituted-1-piperazinyl)dibenzo[b,f][1,4] thiazepine derivative is 11-(4-(2-(2-hydroxyethoxy)ethyl)-1-piperazinyl)dibenzo[b,f][1,4]thiazepine, of Formula VI:

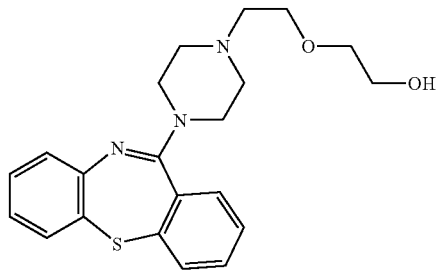

13. The process of claim 12, comprising a step of reacting said 11-(4-(2-(2-hydroxyethoxy)ethyl)-1-piperazinyl)dibenzo[b,f][1,4]thiazepine, of Formula VI, with fumaric acid to obtain quetiapine hemifumarate.

14. The process of claim 1, wherein said piperazine is piperazine, and said 11-(4-substituted-1-piperazinyl)dibenzo[b,f][1,4]thiazepine is 11-(1-piperazinyl)dibenzo[b,f][1,4]thiazepine, of Formula VIII:

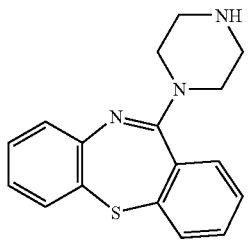

VIII

15. The process of claim 1, wherein said piperazine is 1-(2-hydroxyethyl)piperazine, of Formula IX,

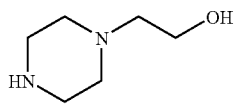

IX and said 11-(4-substituted-1-piperazinyl)dibenzo[b,f][1,4]thiazepine derivative is 11-(4-(2-hydroxyethyl)-1-piperazinyl)dibenzo[b,f][1,4]thiazepine, of Formula X

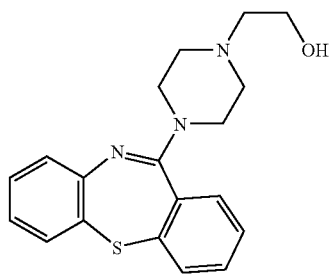

X

16. The process of claim 4, wherein said titanium alkoxide, of formula $Ti(OR)_4$, is added at a rate of 1.5 to 4 equivalents for each equivalent of the Formula II compound.

17. The process of claim 4, wherein said titanium alkoxide, of formula $Ti(OR)_4$, is added at a rate of 2.8 to 3.2 equivalents for each equivalent of the Formula II compound.

18. The process of claim 5, wherein said piperazine, of Formula III, is added at a rate of 1.8 to 2.2 equivalents for each equivalent of the Formula II compound.

19. The process of claim 6, wherein the molar ratio between said titanium alkoxide, of formula $Ti(OR)_4$, and said piperazine, of Formula III, ranges from 1:1.2 to 2.7:1.

20. The process of claim 6, wherein the molar ratio between said titanium alkoxide, of formula $Ti(OR)_4$, and said piperazine, of Formula III, ranges from 1:1.1 to 1.5:1.

21. The process of claim 7, wherein said step is conducted at a temperature ranging from 160° C. to 190° C.

22. The process of claim 7, wherein said step is conducted at a temperature ranging from 165° C. and 175° C.

* * * * *